(12) United States Patent
Wagner (10) Patent No.: US 7,198,760 B1
(45) Date of Patent: Apr. 3, 2007

(54) STERILIZATION CONTAINER

(75) Inventor: Peter Wagner, Starnberg (DE)

(73) Assignee: Wagner GmbH Fabrik Fuer Medizinische Gerate (DE)

( * ) Notice: Subject to any disclaimer, the term of this patent is extended or adjusted under 35 U.S.C. 154(b) by 0 days.

(21) Appl. No.: 09/937,516

(22) PCT Filed: Mar. 21, 2000

(86) PCT No.: PCT/EP00/02502

§ 371 (c)(1),
(2), (4) Date: Mar. 6, 2002

(87) PCT Pub. No.: WO00/57930

PCT Pub. Date: Oct. 5, 2000

(30) Foreign Application Priority Data

Mar. 25, 1999 (DE) ................. 199 13 417

(51) Int. Cl.
*G05D 16/06* (2006.01)
(52) U.S. Cl. ................. 422/108; 422/114; 422/295
(58) Field of Classification Search ............... 422/108, 422/114, 292, 295; 251/89, 89.5, 11
See application file for complete search history.

(56) References Cited

U.S. PATENT DOCUMENTS 4,349,118 A * 9/1982 Sanderson et al. .......... 220/201
5,352,416 A * 10/1994 Wagner ..................... 422/108

FOREIGN PATENT DOCUMENTS

JP         363115022 A  *  5/1988

OTHER PUBLICATIONS hysteresis, The American Heritage® Dictionary of the English Language, Fourth Edition. Houghton Mifflin Company, 2004. Answers.com Aug. 28, 2006. http://www.answers.com/topic/hysteresis.*

* cited by examiner

*Primary Examiner*—Gladys JP Corcoran
*Assistant Examiner*—Sean E Conley
(74) *Attorney, Agent, or Firm*—Ostrolenk, Faber, Gerb & Soffen, LLP (57) ABSTRACT

A sterilization container has a valve arrangement that remains open in a venting phase and is then closed before a pressure difference is compensated for at a predetermined differential pressure. The valve remains closed until the container is opened for the purpose of withdrawing and using the sterilized instruments contained therein. The valve is actuated through a snap disk arrangement, the snap disks of which vault gradually into opposite directions at predetermined temperatures, thereby effecting a defined valve control. The snap disk arrangement is provided in a thermally isolated housing, which prevents a premature back-switching of certain snap disks that could be caused by a cooling-off as a result of the evaporation of condensate.

32 Claims, 11 Drawing Sheets

STERILIZATION CONTAINER

BACKGROUND

The invention relates to a sterilization container having a valve arrangement which permits a media exchange inside a sterilizer right into the vacuum drying phase and closes in the last ventilation phase, so that the vacuum prevailing at this instant in the container interior is maintained and the container remains hermetically sealed, the valve arrangement having a valve body subjected to the flow pressure.

Such sterilization containers, as described, for example, in DE 41 11 075 C2, have the advantage that the material to be sterilized can be kept in the container for a prolonged period without the risk of contamination, since the external atmospheric pressure keeps the container hermetically closed until ventilation is effected at random. The valve body is under spring preloading, which keeps the valve in the open position until the pressure in the sterilizer increases in the last ventilation phase and presses the valve body onto its valve seat, as a result of which the vacuum prevailing in the container at the moment of closing is maintained.

In the valve arrangement, however, the valve body must be reliably prevented from being pressed onto the valve seat prematurely by the inflowing steam, since otherwise no reliable sterilization could take place and the container could even possibly implode. It has been found that the spring preloading of the valve body in the open position cannot reliably prevent premature closing in particular when this valve body subjected to the pressure of the flow medium has a considerable surface extent. The risk of premature closing is there, depending on the load, due to the high inflow velocities. The greater the amount of material to be sterilized which is in the container, the greater is the steam consumption required in the same time. The sterilizer is subjected to a pressure increase controlled with respect to time, i.e. the pressure increases constantly in the environment of the container, and it also penetrates into the container, in which case immediate condensation takes place (gaseous-liquid phase transition releases heat). Accordingly, the container must be "resupplied" with steam, but this steam immediately condenses again, until the heating achieved by constant condensation leads to a situation in which steam can no longer condense.

Thus, if an empty container is sterilized, hardly any more steam is required on the "inside" as on the "outside" (in order to reach 134° C.): the valve is then not substantially loaded with flow pressure.

If a load is sterilized, substantially more steam is "consumed" on the inside—depending on the total weight and the heat capacity of the load: thus substantially more steam—in the same time predetermined by the sterilizer—must therefore [lacuna] through the valve gap than in the empty state. In the case of larger loads, there is therefore the risk of slamming.

In the sterilization containers of the generic type, the valve control is expediently effected via at least one temperature sensor with hysteresis behavior. This temperature sensor may be provided with a snap-disk arrangement, as described in DE 41 11 075 C2. Such a sterilization container, after opening, and after removal of the sterile material, is again available for a renewed sterilization operation without manual valve actuation being necessary. In order to ensure this, the temperature sensor, after removal of the sterilization container from the sterilizer, must automatically switch back again into the original state. In temperature sensors having a snap-disk arrangement, the switching-back is effected by the hysteresis behavior of the thermobimetal. The temperature sensors with snap disks, but also other temperature sensors, are therefore designed in such a way that the switching-back is effected within a temperature range in which the vacuum valve controlled by the sensor is reliably closed, i.e. the switching-back must not be effected before completion of the ventilation phase. In snap-disk arrangements, a temperature of 30 to 50° C. is generally assumed as switch-back temperature, i.e. a temperature which is normally not achieved until after removal from the sterilizer and after cooling of the sterilization container to room temperature.

However, it has been found that these switching temperatures of preferably 35 to 40° C., under certain circumstances, may already be reached during a drying phase inside the sterilizer. This premature cooling may occur during the sterilization of heavy steel loads, since these steel loads produce very large condensate quantities, as a result of which the sensor arrangement may be wetted with condensed steam. If vacuum drying now starts, condensate is re-evaporated, resulting in energy consumption and cooling at those locations where evaporation of the moisture occurs. If such cooling is effected in the region of the temperature sensors, the end of the sterilization operation is simulated, and premature switching-back may be effected, which would result in incorrect switching of the vacuum valve.

SUMMARY

The object of the invention is therefore to ensure reliable vacuum sealing of any desired loads of the sterilization container, even of heavy steel loads.

According to a feature of the present invention, a stop prevents a valve body from closing, and is disabled before or during a venting phase through pressure differentiations. This feature overcomes the above mentioned load- or process-related condensation problems.

According to another feature of the present invention, a temperature sensor is prevented from premature cooling through screening. This feature addresses the above mentioned load- or process-related condensation problems or the problems associated with the premature cooling of the temperature sensor.

The thermal screening also produces reliable screening against moistening due to condensate dripping down and leads to insulation, as a result of which the existing temperature sensors follow the saturated-steam curve in a virtually ideal manner, i.e. cooling to room temperature is effected essentially by convection alone. Instead of the arrangement of the temperature sensors from above/outside on the valve body, the sensors are shifted into the interior of the gas space of the bellows. This results in perfect screening against moistening due to condensate dripping down.

The complete sensor, after switch-on is effected, is now also shut off in a gas-tight manner with respect to the bellows space. The recoil temperature of 95° C. prevails in the sensor space at this instant, so that the temperature sensor cannot continue to cool down inside the sensor space (evaporation can no longer take place); the sensor space itself "conserves" a comparatively high temperature of 95° C. during the entire drying. As a result, it becomes possible to carry out the vacuum drying for as long as desired in a vacuum which is as low as desired without the recoil temperature being reached prematurely inside the sensor space. As a result, premature undesirable switching of the sensor is reliably prevented.

According to a preferred embodiment, which is explained in more detail with reference to the drawing, the temperature sensor preferably provided with snap disks is shifted into the interior of the gas space of a bellows, which results in perfect screening against moistening and heat. In this case, measures are taken which direct the ventilation through the temperature final control element.

This results in the advantage that any desired load of the sterilizer can be dried for as long as desired without the described premature cooling of the temperature sensors being able to lead to a malfunction.

In sterilization technology, work is carried out at different sterilization temperatures of, for example, either 120° C. or 134° C. The sterilization containers have hitherto been equipped with temperature sensors which were adapted only to one of the two common sterilization temperatures and in which malfunctions could not be ruled out if sterilization was carried out with an unmatched steam temperature.

The object of the invention is therefore to also provide a sterilization container having a valve arrangement which reliably carries out the desired switching operations and irrespective of the steam temperature at which sterilization is carried out.

This object is achieved by providing two snap-disk temperature sensors in a snap-disk stack, each having different temperature behaviors. The present invention also features a design and arrangement of the snap disks as provided in the exemplary embodiment described below with reference to the drawing.

The valve arrangement according to the invention may be arranged at any location in the sterilization container, i.e. in the lid or on the side walls of the trough. However, the valve is preferably arranged at the lowest point at the bottom of the trough in such a way that, during the sterilization operation, during which the vacuum valve is open, the condensate water can thus flow off. The draining of condensate therefore permits drying of the container contents without the need for energy-consuming re-evaporation of the condensate. Only in this way does it become possible to produce sterilization containers without having to take into account the thermal conductivity or heat capacity of the material used, so that, for example, containers made of plastic may also be used.

BRIEF DESCRIPTION OF THE DRAWINGS

Exemplary embodiments of the invention are described below with reference to the drawing, in which.

DETAILED DESCRIPTION OF THE PREFERRED EMBODIMENTS

Figure 1:
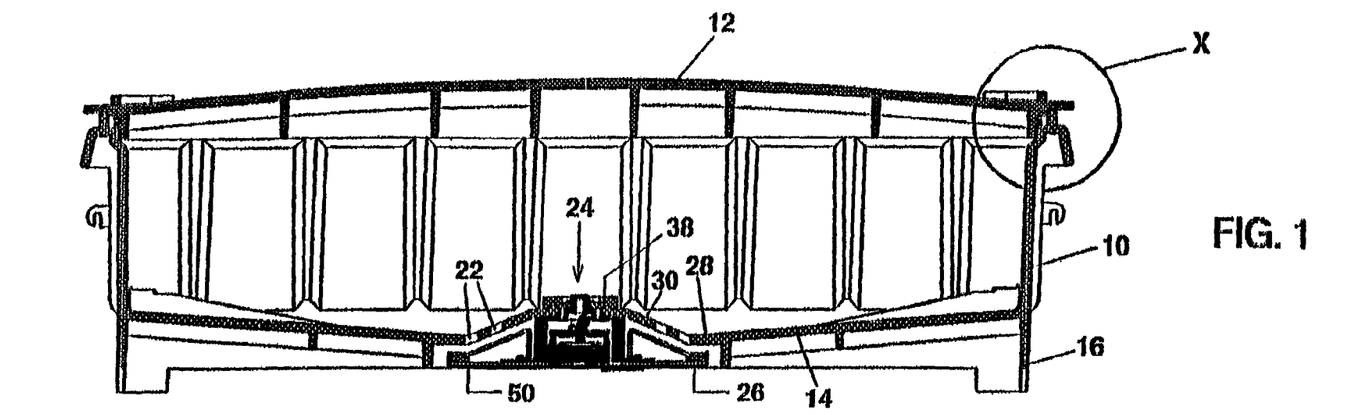
FIG. 1 shows a vertical section of a sterilization container designed according to the invention.
Figure 2:
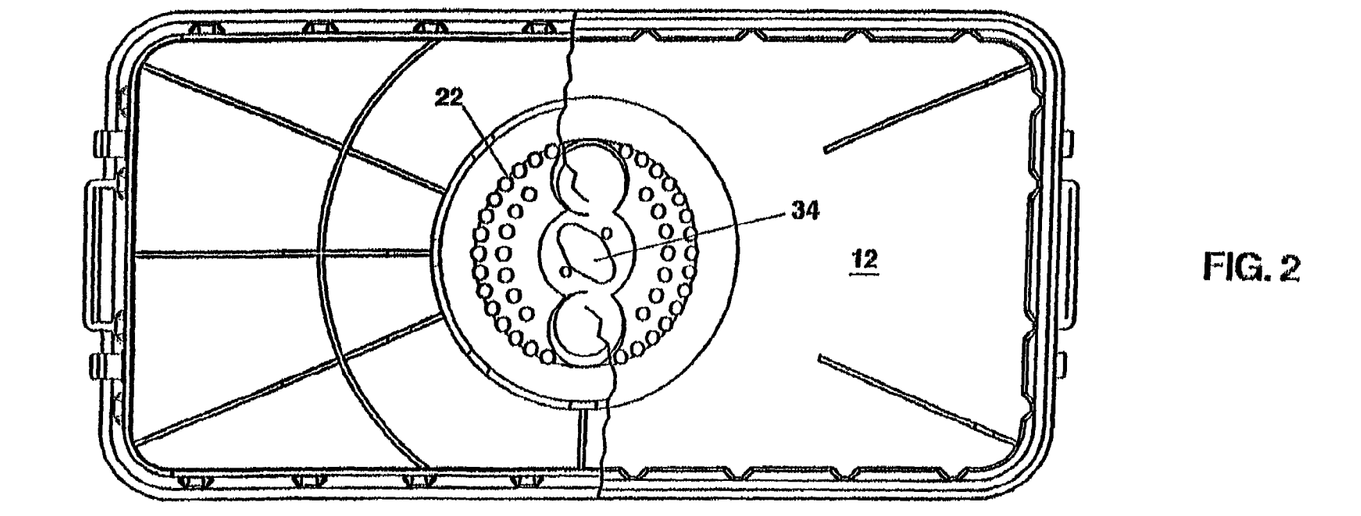
FIG. 2 shows a view of the trough of the sterilization container according to FIG. 1 (in the right-hand part as viewed from above, in the left-hand part as viewed from below)
Figure 3:
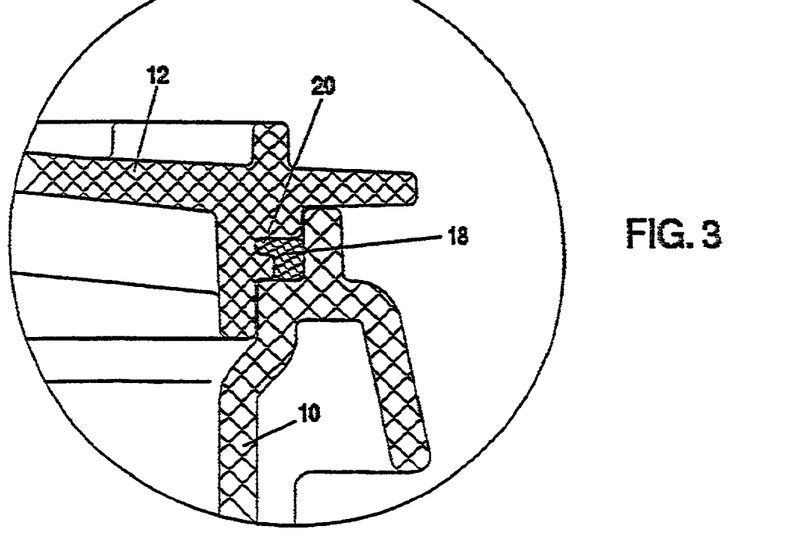
FIG. 3 shows a detail, drawn on an enlarged scale and designated by X in FIG. 1, of the lid seal.

Referring to FIG. 1, the sterilization container consists of the trough 10 and the lid 12. The trough has a sloping bottom 14 and an encircling base frame 16. A sealing ring 18 of L-shaped cross section is arranged between the top rim of the trough 10 and the lid 12 (FIG. 3). This sealing ring, with its inwardly pointing leg, is captively inserted into an encircling groove 20 of the lid 12 and effects a seal downward and outward. The sealing ring 18 accordingly has positive locking in the horizontal, so that adhesive bonding need not be effected, but rather the seal can be exchanged on the spot without any effort. Even if the seal "sticks" slightly to the trough after prolonged mounting, the positive locking enables the lid to be removed without the seal being released from the latter. The seal has a double sealing seat: end-face contact on the one hand (especially at first—when the container is not under vacuum but is only closed with the fasteners), but, when the pressure force is increased (when the pressure difference builds up), specific displacement of the seal into the cavity, enclosed in an encircling manner, in such a way that the vertical surfaces also become tight.

In the deep-set center section, the trough 10 has perforation holes 22 which serve for the media exchange and the outflow of the condensate. A valve arrangement 24 is provided in this center region of the container bottom 14, this valve arrangement 24 having a sealing ring 26 which interacts with an annular valve seat 28 which is formed by the bottom of the trough and lies outside the perforation holes 22, so that the container contents are sealed off from the outside atmosphere after the valve 26, 28 has been closed. The sealing ring is carried by a valve plate subjected to the flow pressure and forms the valve body together with this valve plate.

As can be seen from FIG. 1, the trough bottom 14 has, in the region of the valve arrangement 24, a conical wall section 30 with the perforation holes 22. It is designed in such a way that the valve arrangement can be accommodated above the base area of the base frame 16. Formed in the central flat section 32 is a hole 34 into which a valve cap 36 is inserted from below, this valve cap 36 consisting of a rotationally symmetrical high-grade-steel part and being mechanically secured to the wall section 32 by means of a rotary-lock fastener 38 and by means of a circlip 40. The rotary-lock fastener 38 is an oval rotatable fastener which is held on the valve cap by means of the circlip 40. After the rotary lock 38 is turned by 90°, the valve cap 36 is arrested on the trough bottom. Latching is effected by raised heads 42. A valve-cap flange 44 running under the flat section 32 is welded all-round at the bottom in a gas-tight manner to an axially compressible bellows 46. An outwardly directed annular flange 48 at the lower end of the bellows 46 is welded via an intermediate ring 52 to the valve plate 50 made of high-grade steel. The valve plate 50 carries the sealing ring 26 at its outer periphery. A baffle plate 54 running conically outward and downward under the perforation holes 22 is put onto the valve plate, so that condensate dripping out of the perforation holes 22 is diverted outward and does not collect on the valve plate 50. The valve sealing ring 26 is made of an elastomer, e.g. silicone, and is adhesively bonded or vulcanized in place on the valve plate 50.

Figure 7:
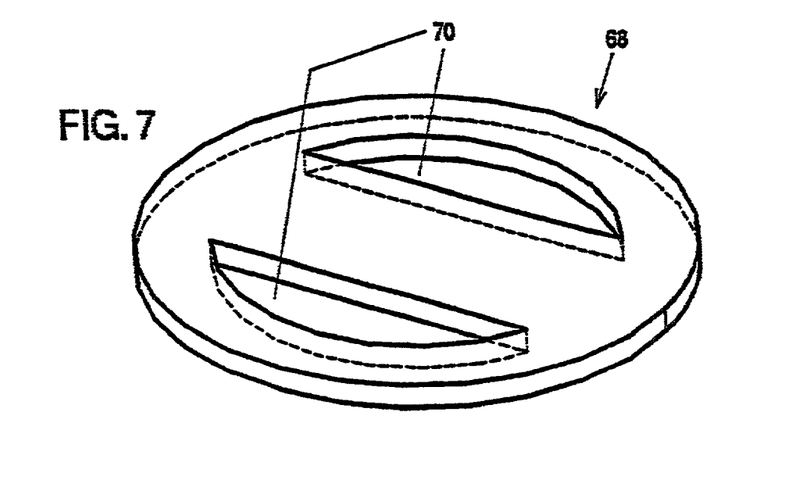
FIG. 7 shows a perspective view of the outlet seal of the valve-control device.

This sealing ring could also be put on the valve seat 28 on the bottom of the trough. The valve plate 50 has a vent opening 56, which is closed by a sealing disk 58, which is pressed on in a sealing manner by a leaf spring 60 welded to the valve plate 50. These parts act as a check valve which permits venting of the valve interior space, i.e. of the space inside the bellows 46. Inside the space enclosed by the bellows 46, a bowl 62 provided with an internal thread is welded in place on the valve plate 50. The base of this bowl 62 has a center opening 64 which is in alignment with a ventilation opening 66 in the valve plate 50. This ventilation opening 64, 66 is covered by an outlet sealing disk 68, which lies on the base of the bowl 62 and is designed according to FIG. 7. It has two openings in the form of segments of a circle, between which the web covering the ventilation opening 64, 66 lies.

The annular wall 72, provided with an external thread, of a lid 74 is screwed into the internal thread of the bowl 62. The lower annular end face of the annular wall 72 is restrained in a sealing manner against the rim of the outlet sealing disk 68. This sealing disk 68 accordingly has a double function by virtue of the fact that, on the one hand, it closes the ventilation opening 64, 66 when there is internal positive pressure in the valve and, on the other hand, it seals the parts 62, 72 screwed to one another.

Figure 6:
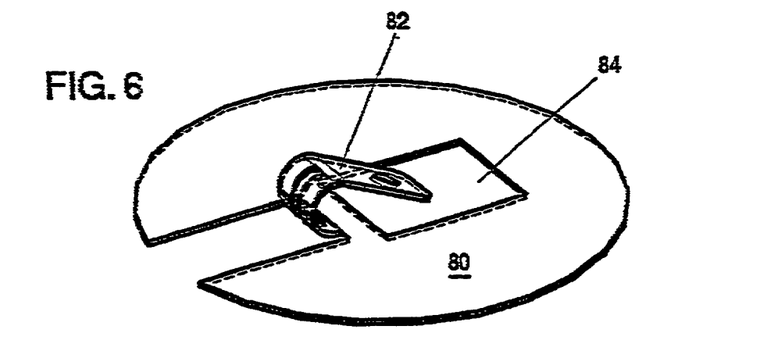
FIG. 6 shows a perspective view of the cover plate, carrying the control members, of the valve-control device.

The lid 74 has a center hole 76 with a recess for a sealing ring 78. The ventilation of the valve interior space is effected via this center opening. Welded in place on the lid 74 is a spring-steel plate 80, from which a blocking spring 82 is stamped and, in the manner which can be seen from FIG. 6, is bent in such a way that it overlaps a cutout 84 of the disk 80, this cutout 84 lying above the center opening 76 of the lid. This blocking spring 82, designed as a leaf spring, carries a blocking pin 86 which is notched in a V-shape and prevents the slamming of the valve by flow pressure, as will be described in detail further below. The blocking pin 86 is connected to the leaf spring 82 via a press-in pin 88, which projects downward into the center opening 76 and interacts with a polished valve ball 90, the valve seat of which is formed by the sealing ring 78.

The housing formed by bowl 62 and lid 74 and enclosing the temperature sensor forms, together with the valve cap 36 and the bellows 46, thermal screening for the temperature sensor and prevents ingress of condensate dripping down and thus premature switching of the snap-disk temperature sensor. This could be realized with only one snap-disk type which keeps the valve open, closes the valve when the control temperature "hot" is reached (venting via the check valve) and only then opens again—protected by the insulated fitting—after sealing (vacuum) and cooling of the container have been effected (in order to prepare the valve for the next use).

The following switching temperatures of the temperature sensor, for example, would be conceivable:

134° C. during heating/30–50° C. during cooling: this valve would "function" during every sterilization program which reaches 134° C.

Disadvantage: it would not operate if, for example, a 120° C. program is run (for it would of course then never switch "ON").

120° C. during heating/30–50° C. during cooling: this valve would function in a 120° C. program, and also to a limited extent in a 134° C. program, although involving risks: if the valve closes at 120° C., a further pressure increase in the gas space of the bellows is no longer possible (only its venting . . . ); but it is not until 120° C. that a pressure of 2.1 hPa prevails (saturated-steam curve). If a container is now sterilized in a 134° C. program, a further pressure increase to 3.2–3.4 hPa is effected. This pressure increase (difference is 1.1–1.3 hPa) would compress the bellows, and could therefore not penetrate into the container, with the result that either the correct sterilization conditions are not reached inside the container or that the container does not withstand the pressure difference and implodes.

134° C. and 120° C. programs are the two standard temperature levels in hospital sterilization. A user therefore ought to have different valves (for 120° C. or 134° C. level) and also to attach or exchange these valve before use. This is conceivable, but awkward and susceptible to errors. The snap-disk arrangement described below avoids this disadvantage by the valve being designed in such a way that it can be used at all the common sterilization levels.

Figure 5:
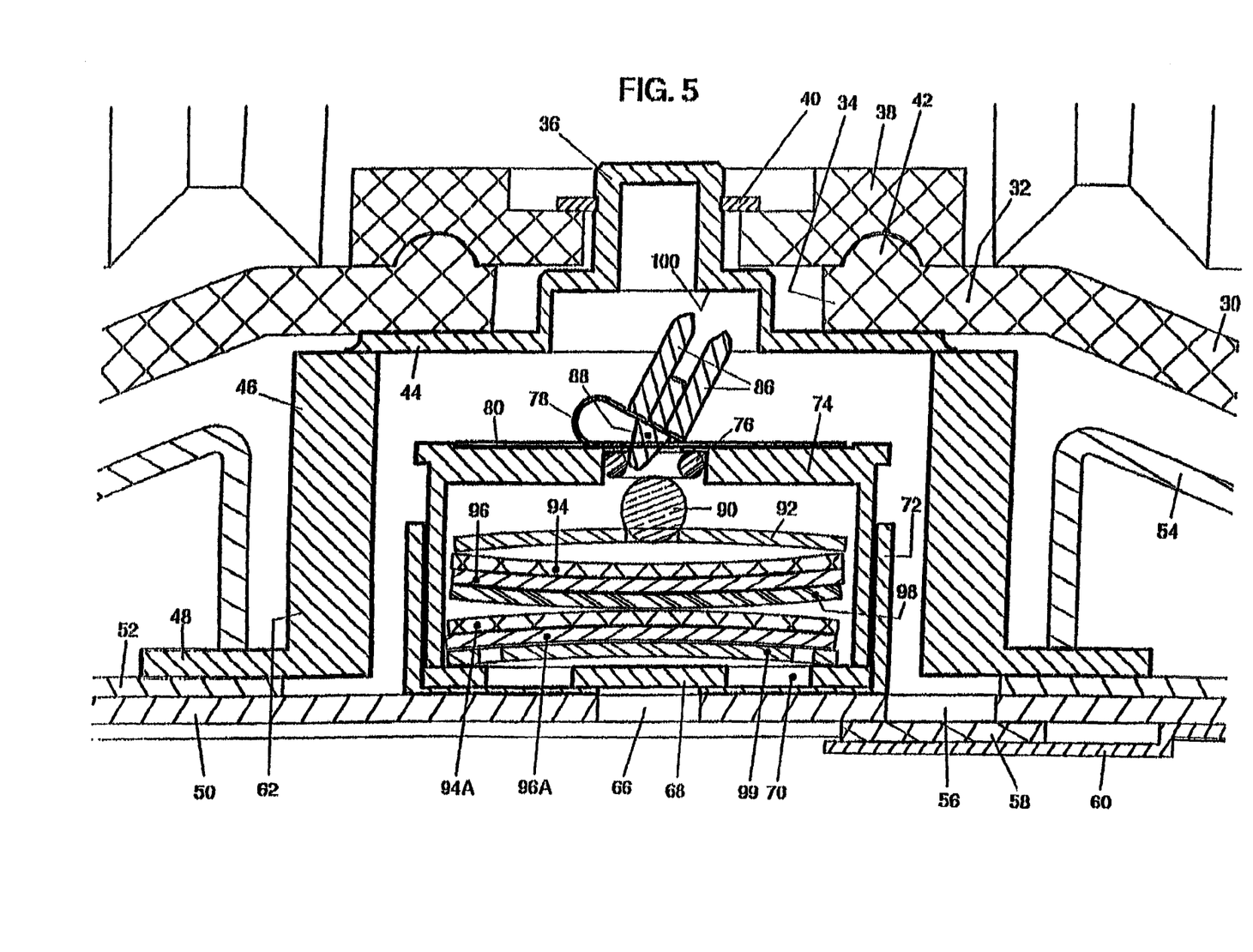
FIG. 5 shows a sectional view, drawn on an enlarged scale, of the valve-control device in the position according to FIG. 4.

The valve ball 90 is carried by a high-grade-steel disk which runs convexly upward in a spherical segment shape and to which it is welded. This high-grade-steel disk 92 retains its shape irrespective of temperature and pressure changes and is displaced merely within the space defined by the annular wall 72 by interacting with the snap disks described below. These snap disks are made of thermobimetal and are characterized in that they switch over into their opposite curvature state at a predetermined heating temperature and, affected by hysteresis, snap back during cooling at a lower switching temperature. In FIG. 5, the snap disks described below are depicted in their curvature state which they assume at room temperature. The snap disk 94 adjacent to the high-grade-steel disk 92 is curved in the opposite direction to the steel disk 92 and is upwardly concave. This snap disk 94 typically has the following switch-over temperatures:

during heating, the snap disk 94 snaps over from the concave position into the convex position at 115° C. During cooling, it snaps back from the convex position into the concave position at 95° C.

Adjacent to the snap disk 94 is a further snap disk 96 having a switching characteristic which is different from the switching characteristic of the snap disk 94. The fitted position of the snap disk 96 corresponds to that of the snap disk 94 and it bears convexly upward in full-face contact with the snap disk 94. The thermobimetal snap disk 96 typically has the following switching temperatures: during heating, it snaps over from the concave position into the convex position at 117° C. During cooling, it snaps back from the convex position into the concave position at 35 to 50° C.

Adjacent to the snap disk 96 is a further high-grade-steel disk 98 which is of upwardly concave design and corresponds to the curvature of the inserted snap disks; it does not change its shape, only its position.

Adjacent to the high-grade-steel disk 98 is a snap disk 94A curved convexly upward and having the same switching characteristic as the snap disk 94. Adjacent to this snap disk 94A is a snap disk 96A which is likewise curved convexly upward and has the same switching characteristic as the snap disk 96. The snap disk 96A is supported by a further dimensionally stable high-grade-steel disk 99 which is curved convexly upward and corresponds in its curvature exactly to the curvature of the snap disks. This high-grade-steel disk is provided with holes for improving the steam inlet and is supported at the peripheral rim on the outlet sealing disk 68. The intermediate ring 52 forms a shim for providing a distance between the annular flange 48 of the bellows 46 and the valve plate 50 and is connected to these parts in each case in a gas-tight manner by welding, adhesive bonding or screwing.

In the drawing, for the sake of clarity, in each case only the snap disk determining the function is shown. In practice, it may be expedient to use in each case a plurality of identical snap disks fitted in the same direction.

Figure 4:
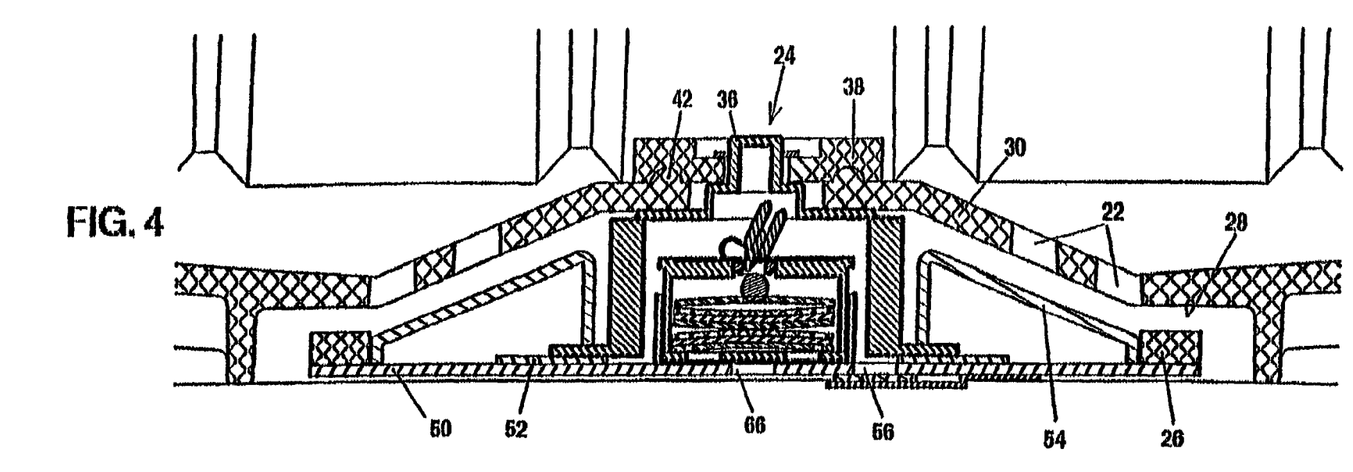
FIG. 4 shows a side view of the valve, inserted into the bottom of the trough, in the open position.

The function of the valve arrangement 24 is described below with reference to FIGS. 4 to 13:

The position of the snap disks which is shown in FIGS. 4 and 5 is maintained during heating up to 115°. At 115° C., the snap disks 94 and 94A switch over into their opposite curvature position according to FIG. 10. The overall height and thus the position of the valve ball 90 does not change in the process.

Figure 11:
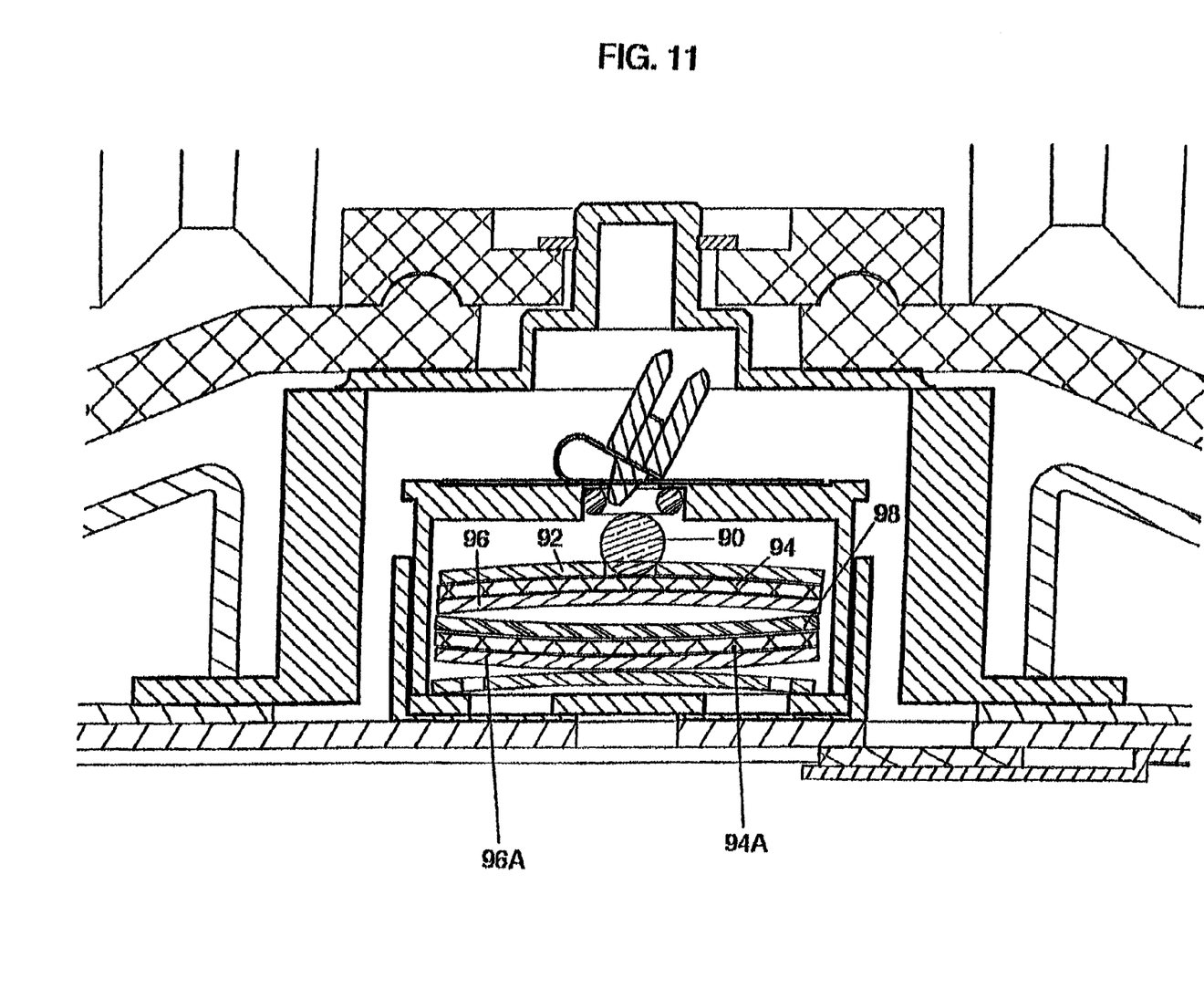
FIG. 11 shows the valve-control device in a sectional view during a temperature increase after reaching a second temperature (of, for example, 117° C.)

When the second switch-over temperature of 117° C. is reached, the snap disks 96 and 96A additionally switch over into their opposite curvature position, as can be seen from FIG. 11. The overall height of the stack and the position of the valve ball 90 remain unchanged, so that the valve ring 26 remains lifted from its valve seat 28, i.e. the valve remains open, so that the media exchange can continue to be effected without hindrance.

Figure 8:
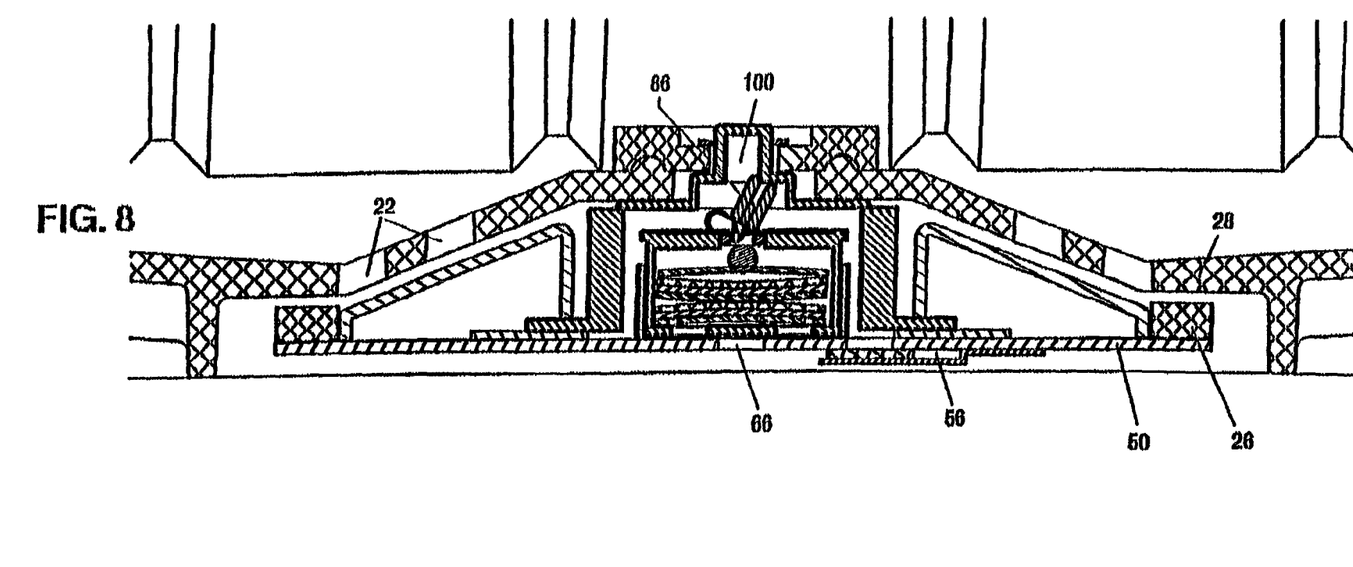
FIG. 8 shows a view of the valve body shifted into the open position against a stop.
Figure 9:
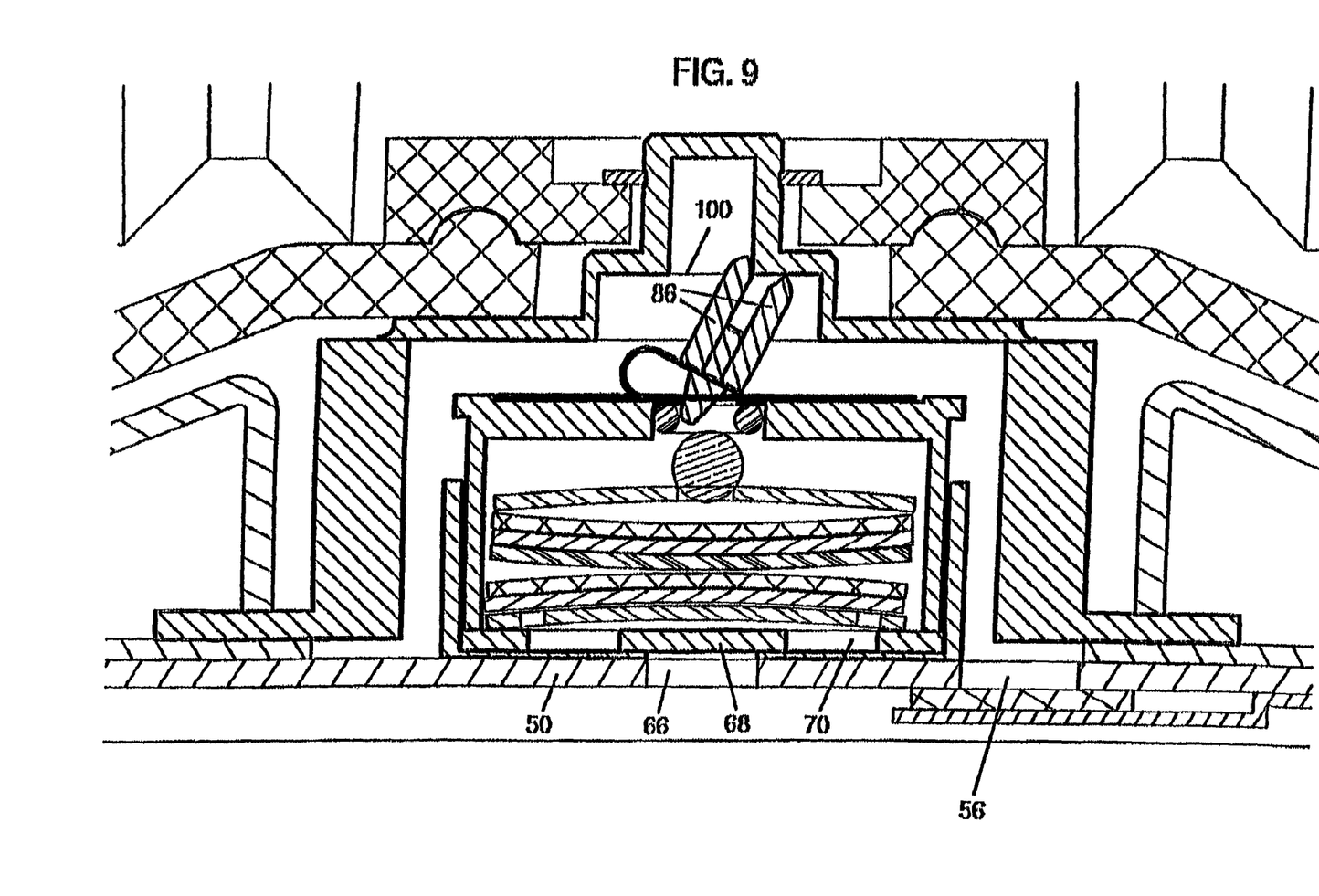
FIG. 9 shows, on an enlarged scale, a view corresponding to FIG. 8.
Figure 10:
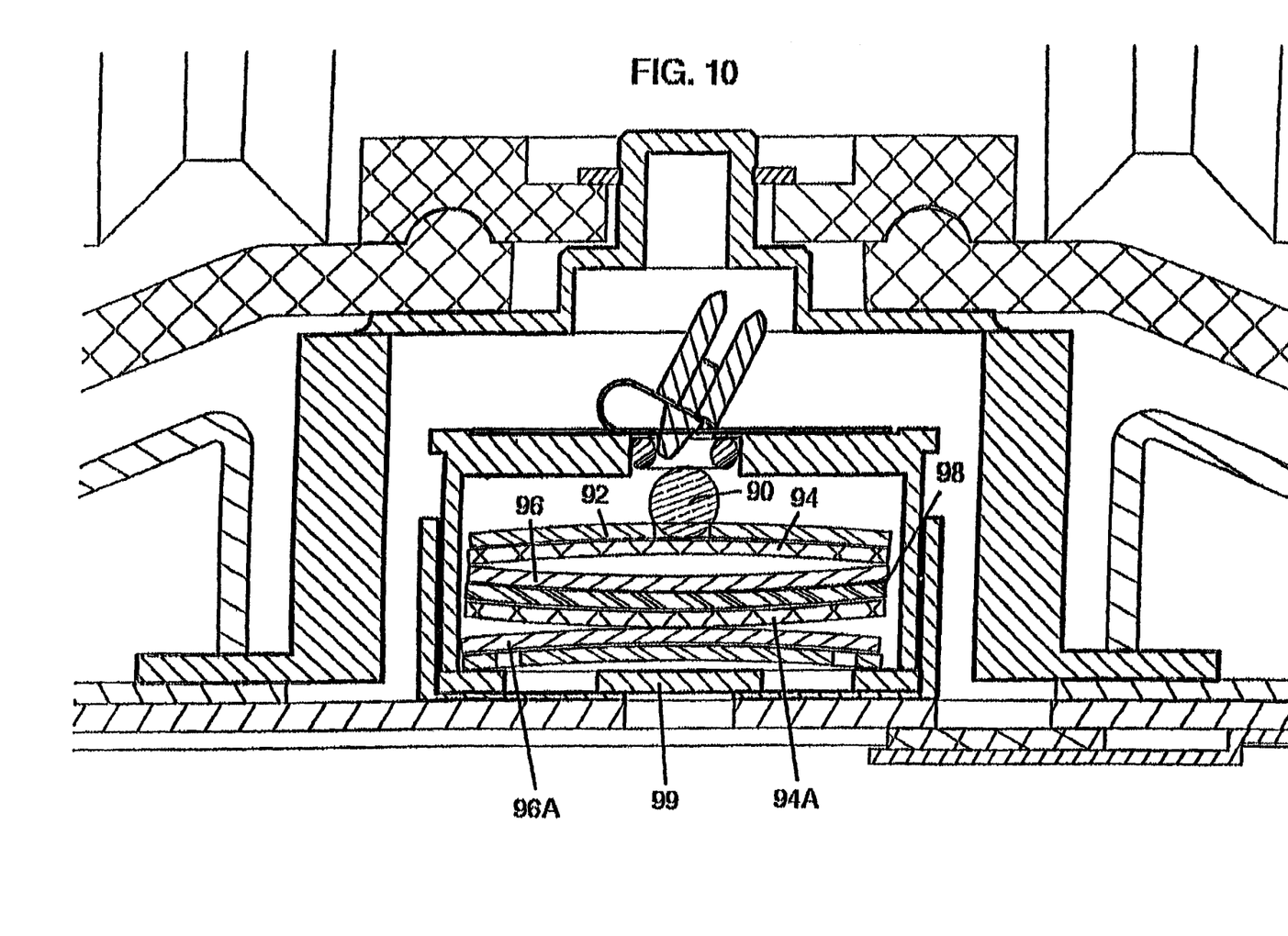
FIG. 10 shows the valve-control device in a view after a temperature increase to a first temperature (of, for example, 115° C.)

According to the invention, measures are taken in order to hold the valve in the open position even when, during the sterilization operation, a flow pressure loads the valve body formed by the valve plate 50, this flow pressure attempting to close the valve against spring preloading. FIGS. 8 and 9 show that a pressure acting on the valve plate 50 from the bottom upward has displaced the valve plate and the parts carried by it only until the blocking pin 86 held in the inclined position by the spring 82 strikes the step 100 of the valve cap 36. This stop position can be seen from FIGS. 8 and 9. A flow gap between the valve seat 28 and the valve ring 26 is also maintained in this position, so that the media exchange can continue to take place without hindrance. Slamming of the container is therefore reliably prevented, so that any desired loads can be sterilized in sterilizers which are as fast as desired without it being possible for the container to be destroyed.

Figure 12:
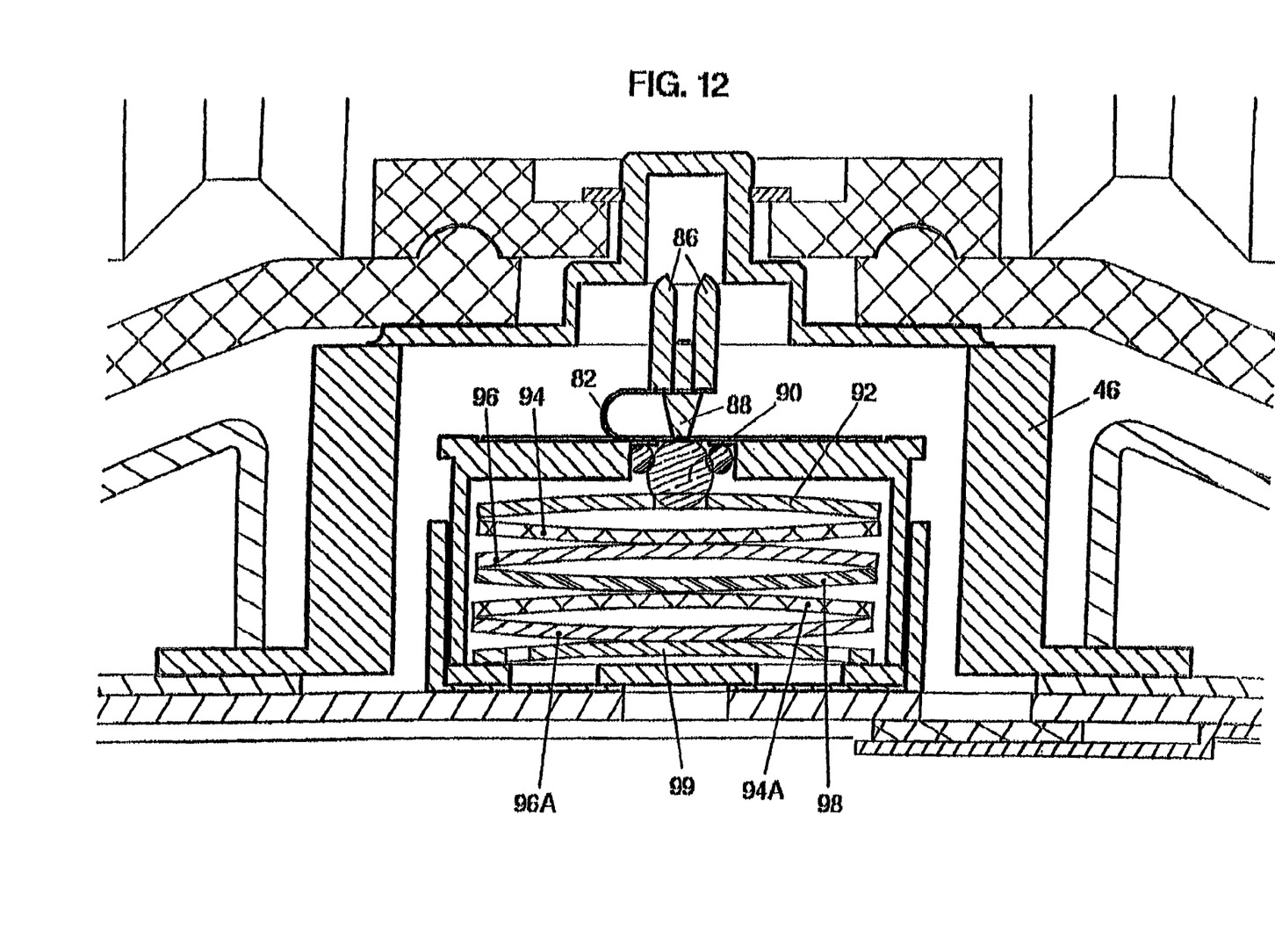
FIG. 12 shows a sectional view of the valve-control device after a cooling phase.

During the cooling phase, the snap disks 94 and 94A switch over into the position according to FIG. 12 at about 95° C., whereas the curvature of the snap disks 96 and 96A still remains unchanged. This results in expanding of the snap-disk stack and thus in lifting of the valve ball 90, which in this position according to FIG. 12 bears against the sealing ring 78 and closes off the valve space from above. During its upward movement, the ball 90 has lifted the blocking pin 96 via the press-in pin 88 and, as can be seen from FIG. 12, straightened it up, so that the blocking pin can run freely into the valve cap 36. During the pressure drop in the sterilizer, the external pressure progressively decreases relative to the internal pressure in the container and in the valve space, and pressure compensation is effected via the valve 26, 28, which is still open, it being possible for the pressure compensation inside the valve chamber to be effected via the check valve 58 or the vent opening 56. Further evaporation—and thus vacuum cooling—inside the temperature sensor can now no longer occur, so that premature, undesirable switching of the sensor is reliably prevented.

Figure 13:
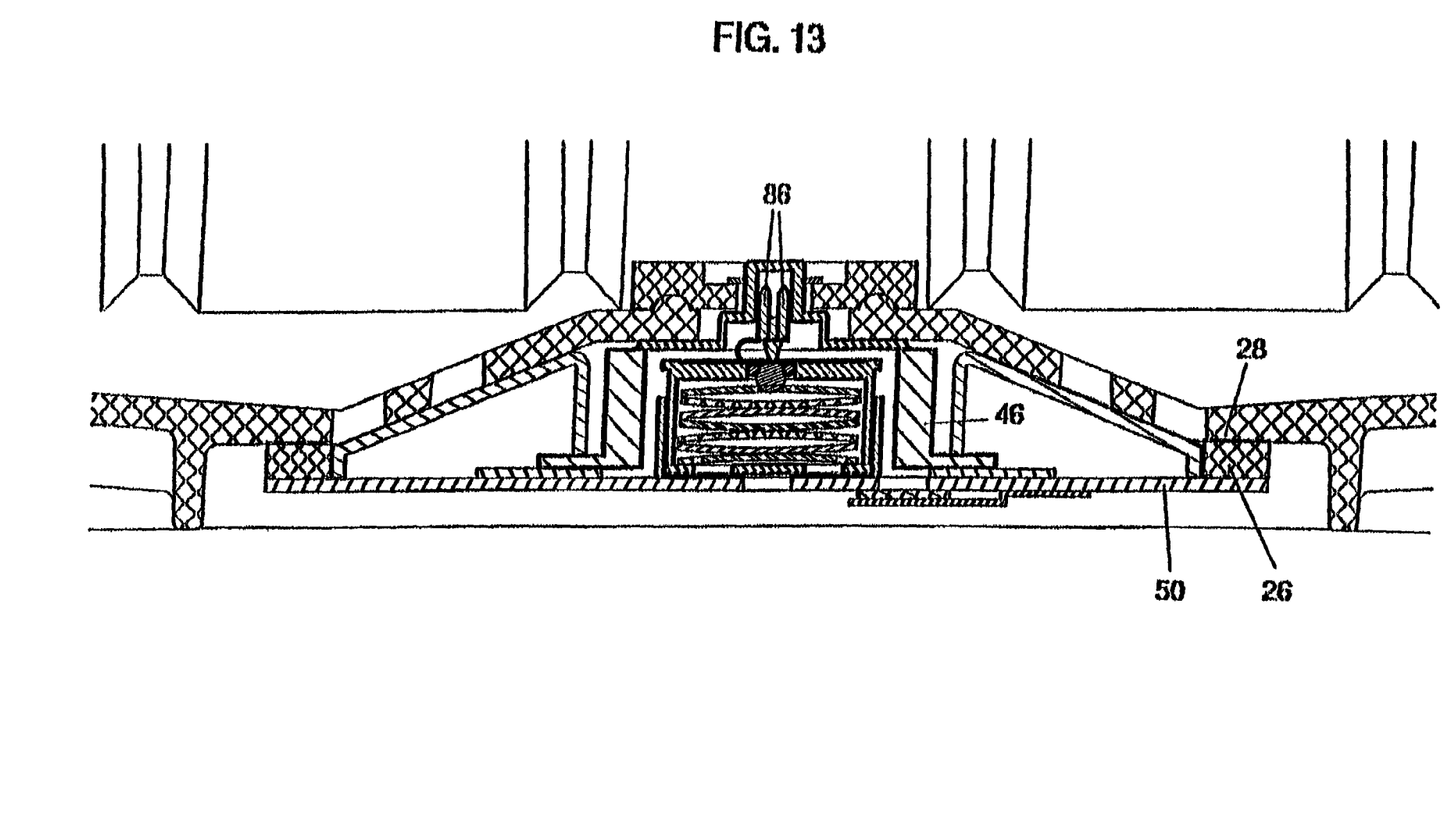
FIG. 13 shows a sectional view of the valve in the closed position.

As soon as the pressure in the sterilizer increases again in the last ventilation phase, the bellows is compressed to an increasing extent as a result of the pressure difference which builds up and the valve 26, 28 is closed, in which case the blocking pin 86, as can be seen from FIG. 13, can run into the interior of the valve cap 36. During this operation, the bellows 46 is compressed. This closed position of the valve 26, 28 is maintained during the further cooling and also after removal of the sterilization container from the sterilizer, since a vacuum is maintained in the interior of the sterilization container and the atmospheric pressure keeps the valve closed. By appropriate dimensioning of the valve gap or of the bellows (cross section and spring rate), the level of the trapped vacuum can be varied within wide limits.

During cooling to their switching temperature (e.g. 35 to 50° C.), the snap disks 96, 96A snap over into their opposite curvature position, as a result of which the valve ball 90 is lifted from its seat. In the process, the valve space is ventilated via the ventilation opening 66, but the container interior space is not ventilated. The valve arrangement itself remains in the closed position until the atmospheric pressure can penetrate into the sterilization container via an additional ventilation valve, not shown in the drawing, and a filter connected upstream of the latter. As a result of the spring action of the bellows 46 and due to gravitational force, the valve arrangement then returns into the position according to FIGS. 4 and 5, and the sterilization container can be used for the next sterilization operation without manual manipulation.

Figure 14:
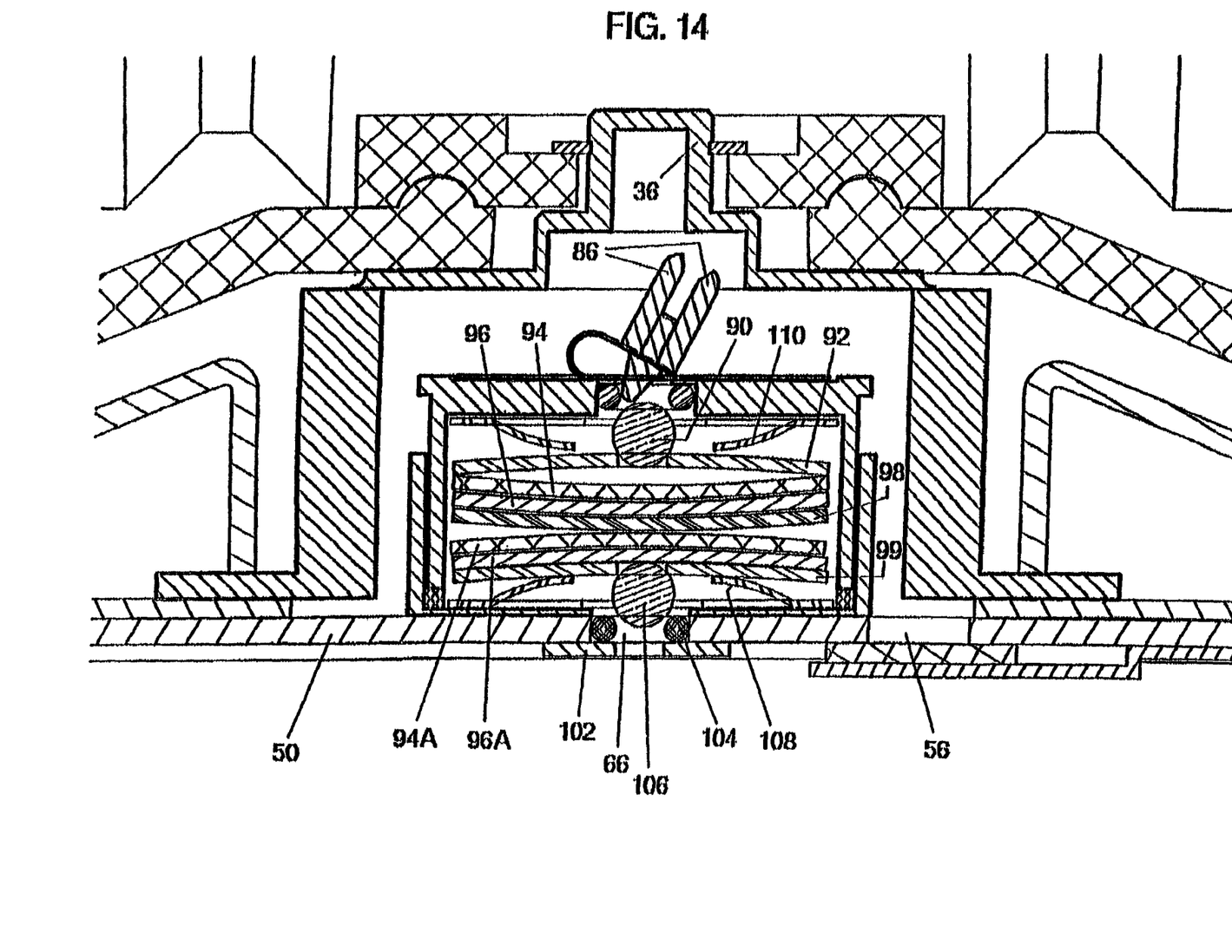
FIG. 14 shows a sectional view of a second embodiment of the valve-control device in an operating position according to FIG. 5.
Figure 15:
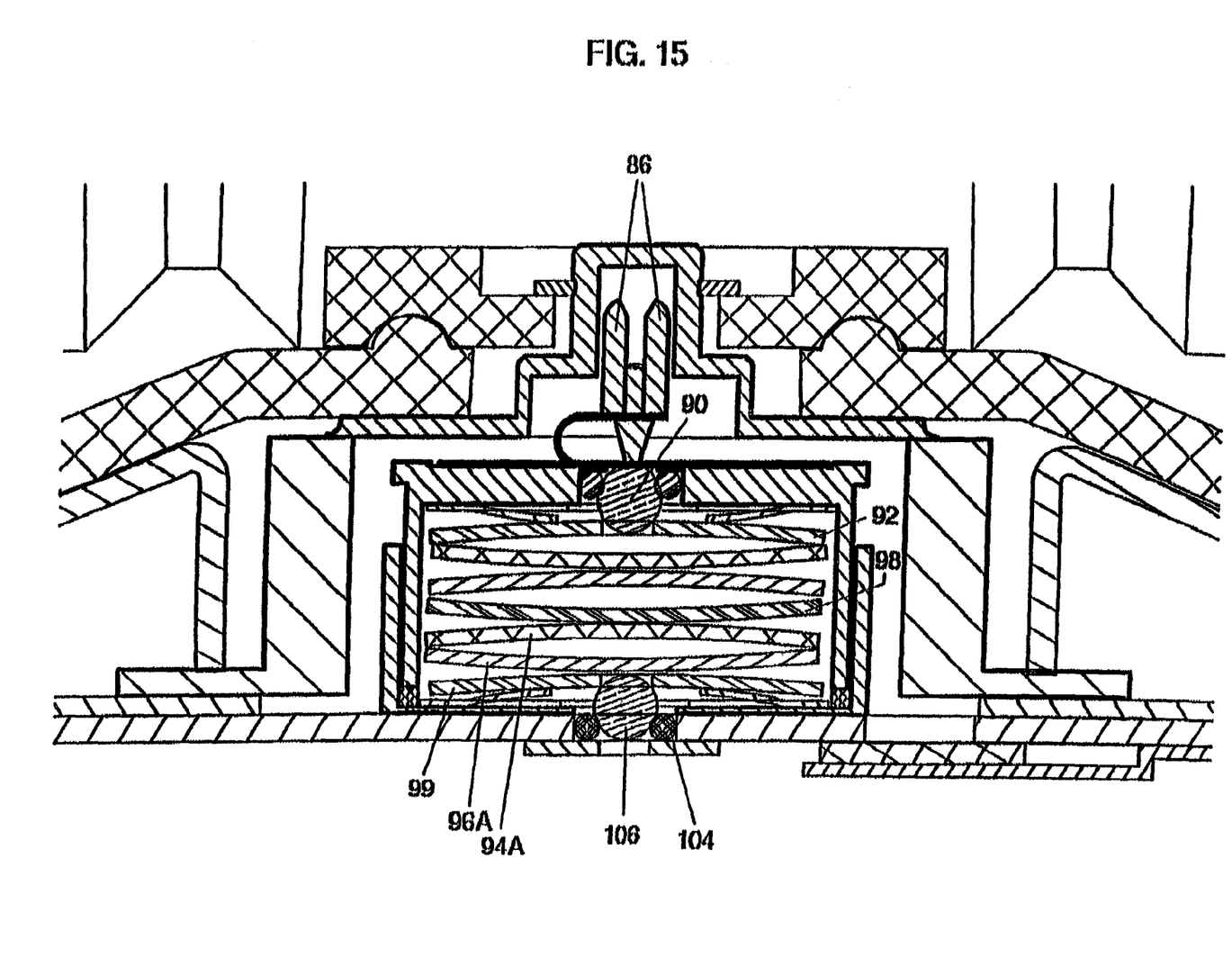
FIG. 15 shows a sectional view of the valve-control device according to FIG. 14 in the valve closed position according to FIG. 13.

A further exemplary embodiment is shown in FIGS. 14 and 15. The function of the valve arrangement shown here corresponds essentially to the function in the case of the embodiment shown according to FIGS. 1 to 13. The valve arrangement is modified compared with the exemplary embodiment described above inasmuch as a second ball valve is arranged instead of the outlet sealing disk 68. This ball valve consists of a valve-seat ring 104 which is inserted into the ventilation opening 66, is secured by a disk 102 and interacts with a valve ball 106 which is welded to the convexly curved high-grade-steel disk 99. This disk 99 is preloaded by springs 108, as a result of which the valve ball 106 is lifted from its seat. Further springs 110 act on the top high-grade-steel disk 92, as a result of which the valve ball 90 is preloaded in the open position. This causes the ventilation opening 66 to be constantly open while the valve is open. It is not until switch-over is effected into the position according to FIG. 15, which corresponds to the position according to FIG. 12, that the ventilation opening is closed. The difference compared with the first exemplary embodiment accordingly consists in the fact that, after the switching of the snap disks, the snap-disk housing is completely shut off in both directions.

LIST OF DESIGNATIONS

10 Trough
12 Lid
14 Sloping bottom
16 Base frame
18 Sealing ring 20 Groove
22 Perforation holes
24 Valve arrangement
26 Sealing ring, valve ring
28 Valve seat
30 Conical wall section
32 Flat section
34 Hole
36 Valve cap
38 Rotary-lock fastener
40 Circlip
42 Heads
44 Valve-cap flange
46 Bellows
48 Annular flange
50 Valve plate
52 Intermediate ring
54 Baffle plate
56 Vent opening
58 Sealing disk
60 Leaf spring
62 Bowl
64 Center opening
66 Ventilation opening
68 Outlet sealing disk
70 Openings
72 Annular wall
74 Lid
76 Center opening
78 Sealing ring
80 Spring-steel plate
82 Blocking spring
84 Cutout
86 Blocking pin
88 Press-in pin
90 Valve ball
92 High-grade-steel disk
94, 94A Snap disk
96, 96A Snap disk
98 High-grade-steel disk
99 High-grade-steel disk
100 Step
102 Disk
104 Valve-seat ring
106 Valve ball
108 Springs
110 Springs

The invention claimed is:

1. A sterilization container for holding items to be passed through a sterilization process that includes a conditioning phase, a high temperature sterilization exposure phase, a vacuum drying phase and a ventilation phase, the container capable of remaining hermetically sealed and maintaining a vacuum established during the sterilization process;
the container having a valve arrangement permitting a medium exchange between an inside and an outside of the sterilization container during the sterilization process, the valve arrangement comprising:
an open position of the valve arrangement to permit the exchange of the medium and a closed position of the valve arrangement to prevent the exchange of the medium;
a valve body movable in response to a pressure increase outside the container and outside the valve arrangement, to urge the valve arrangement to the closed position;
a stop in the valve arrangement, the stop having a stop position to prevent the valve arrangement from moving to the closed position; and
a temperature sensor coupled to the stop and operable to urge the stop away from the stop position based on a set temperature without also causing the valve to close the container.

2. The sterilization container according to claim 1, wherein the temperature sensor exhibits hysteresis based on temperature.

3. A sterilization container for holding sterilized items to be passed through a sterilization process in a sterilizer that includes a conditioning phase, a high temperature sterilization exposure phase, a vacuum drying phase and a ventilation phase, the container capable of remaining hermetically sealed and maintaining a vacuum established during the sterilization process; the container having a valve arrangement permitting an exchange of a medium between the sterilizer and the sterilization container during the sterilization process, the valve arrangement comprising:
an open position of the valve arrangement to permit the exchange of the medium and a closed position of the valve arrangement to prevent the exchange of the medium; and
a temperature sensor in the valve arrangement and the sensor being enclosed in an enclosure separately from the container, the sensor enclosure includes a valve closure; the valve closure to the sensor enclosure being closable independently of the valve arrangement to the container, which insulates the temperature sensor from a sterilizer environment in which the container is disposed, wherein the temperature sensor is protected from premature cooling;
the temperature sensor being operable to prevent the valve arrangement from moving to the closed position until a set temperature cycle of the sterilizer is complete.

4. The sterilization container according to claim 3, wherein the temperature sensor exhibits hysteresis based on temperature.

5. The sterilization container according to claim 1, wherein the temperature sensor further comprises:
a snap-disk stack having a plurality of snap disks each having a shape that varies responsive to temperature changes; and
at least two of the snap-disks in the snap-disk stack having different respective temperature behaviors.

6. The sterilization container according to claim 1, further comprising:
a recess at a bottom portion of the sterilization container; and
the valve arrangement being located in the recess and operable to permit condensate formed during the sterilization process to drain from the bottom portion through the valve arrangement.

7. The sterilization container according to claim 6, further comprising:
a central wall section in the bottom portion and having a conical shape that is tapered inward in an upward direction;
perforation openings in the central wall section to permit condensate to drain through the perforation openings when the valve arrangement is in the open position;
an annular valve seat surrounding the perforation openings; and
the valve body having a valve plate and a valve ring on the valve plate, the valve ring cooperating with the annular valve seat to seal the sterilization container.

8. The sterilization container according to claim 7, wherein the temperature sensor further comprises:
- a snap-disk stack having a plurality of snap disks each having a shape that varies responsive to temperature changes; and
- at least two of the snap-disks in the snap-disk stack having different respective temperature behaviors;
- a housing in a center section of the valve plate and accommodating the snap-disk stack; and the valve arrangement further comprises:
- a valve ball coupled to the snap-disk stack and movable in response to changes in the shape of the snap disks in the snap-disk stack; and
- a valve-seat ring in the housing and cooperative with the valve ball to form a seal with the valve ball when the valve ball is moved in response to changes in the shape of the snap disks in the snap-disk stack.

9. The sterilization container according to claim 8, further comprising:
- a bellows having an upper and a lower end and arranged around the housing in the valve arrangement;
- a valve cap in the valve arrangement releasably fastened to the bottom portion of the sterilization container; and
- the lower end of the bellows being connected to the valve plate and the upper end of the bellows being secured to the valve cap.

10. The sterilization container according to claim 9, further comprising:
- an opening in the bottom portion of the sterilization container; and
- a protrusion on the valve cap being shaped to fit in the opening and be releasably fixed in place.

11. The sterilization container according to claim 8, further comprising:
- a housing lid on an upper portion of the housing in the valve arrangement; and
- a blocking spring on the housing lid and having a blocking pin, the blocking spring urging the blocking pin into a position to cooperate with the stop.

12. The sterilization container according to claim 11, wherein the blocking spring is positioned to permit the valve ball to act against the urging of the blocking spring to shift the blocking pin to a release position to prevent cooperation between the blocking pin and the stop when the valve ball is moved in response to changes in the shape of the snap disks in the snap-disk stack.

13. The sterilization container according to claim 8, further comprising:
- a ventilation outlet in a bottom portion of the housing for ventilating the housing;
- a ventilation opening in the valve plate communicating with the ventilation outlet; and
- an outlet sealing disk cooperating with the ventilation outlet to form a check valve in the housing.

14. The sterilization container according to claim 9, further comprising:
- a vent opening in the valve plate communicating with a region enclosed by the bellows;
- a vent sealing disk cooperating with the vent opening to form a check valve in the region enclosed by the bellows; and
- a leaf spring on the valve plate arranged to provide preloading to urge the vent sealing disk to a seal position to close the vent opening.

15. The sterilization container according to claim 13, further comprising:
- two coaxial cup-shaped parts, one cup-shaped part being screwed within the other cup-shaped part to form the housing in the valve arrangement; and
- an annular end of the one cup-shaped part contacts the outlet sealing disk.

16. The sterilization container according to claim 11, further comprising an extension of the blocking pin cooperating with the valve ball to shift the blocking pin to a release position against the urging of the blocking spring when the valve ball is moved.

17. The sterilization container according to claim 8, further comprising:
- a ventilation outlet in a bottom portion of the housing for ventilating the housing;
- a ventilation opening in the valve plate communicating with the ventilation outlet; and
- another valve ball coupled to the snap-disk stack and positioned to block the ventilation outlet in response to changes in the shape of the snap disks in the snap-disk stack.

18. The sterilization container according to claim 7, further comprising a baffle plate having a conical shape tapered inward and upward on the valve plate below and beneath the perforation openings for deflecting condensate drained through the perforation openings.

19. The sterilization container according to claim 5, wherein the snap disks having different respective temperature behaviors are paired together and the paired snap disks have a same curvature configuration at room temperature.

20. The sterilization container according to claim 19, further comprising two snap-disk pairs in the snap-disk stack, one pair being curved concavely upward in the snap-disk stack and another pair being curved convexly upward in the snap-disk stack.

21. The sterilization container according to claim 20, further comprising a steel disk curved convexly upward with temperature and pressure resistant curvature on a top of the snap-disk stack and having the valve ball arranged on a center part of the steel disk.

22. The sterilization container according to claim 20, further comprising:
- a first steel disk curved convexly upward with temperature and pressure resistant curvature supporting the snap-disk stack; and
- a second steel disk curved concavely upward with temperature and pressure resistant curvature and disposed between the two snap-disk pairs.

23. The sterilization container according to claim 5, wherein one of the snap-disks in the snap-disk stack has a temperature behavior of changing shape at about 115° C. during heating and changing shape under hysteresis at about 95° C. during cooling.

24. The sterilization container according to claim 5, wherein one of the snap disks in the snap-disk stack has a temperature behavior of changing shape at greater than about 115° C. during heating and does not change shape again until cooled to about 50° C. under hysteresis.

25. The sterilization container according to claim 24, wherein the one snap disk changes shape at about 117° C. during heating.

26. The sterilization container according to claim 24, wherein the one snap disk does not change shape again until cooled in the range of from about 30° C. to about 50° C. under hysteresis.

27. The sterilization container according to claim 17, further comprising:

a steel disk curved convexly upward with temperature and pressure resistant curvature supporting the snap-disk stack; and the another valve ball arranged on the steel disk.

28. The sterilization container according to claim 9, further comprising:

a lower annular flange on the bellows extending outward from the bellows; and a distance piece between the lower annular flange and the valve plate to connect the bellows to the valve plate.

29. The sterilization container according to claim 17, further comprising:

a rim of the sterilization container having a trough with a vertical surface and a horizontal surface;

a container lid shaped to cooperate with the rim to enclose a top of the sterilization container;

a circumferential groove in the container lid;

a sealing ring arranged on a circumferential edge of the container lid and having a leg arranged on a radially inward portion of the sealing ring;

the leg being shaped to be received in the groove of the container lid; and the sealing ring provides a seal between the container lid and the vertical and horizontal surfaces of the trough.

30. The sterilization container according to claim 1, wherein the valve arrangement in the closed position completely prevents the exchange of the medium between outside and inside the container and wherein the container includes no other elements enabling the exchange of medium when the valve arrangement is in the closed position.

31. The sterilization container according to claim 1, wherein the temperature sensor is enclosed in an enclosure separately from the container, the sensor enclosure includes a valve closure; the valve closure to the sensor enclosure being closable independently of the valve arrangement to the container, which insulates the temperature sensor from a sterilizer environment in which the container is disposed, wherein the temperature sensor is protected from premature cooling;

the temperature sensor being operable to prevent the valve arrangement from moving to the closed position until a set temperature cycle of the sterilizer is complete.

32. The sterilization container according to claim 1, wherein the valve arrangement when open is urged to a closed position after removal of the stop only by the pressure increase around the container and the valve arrangement.

* * * * *